US008257491B2

(12) United States Patent
Park et al.

(10) Patent No.: US 8,257,491 B2
(45) Date of Patent: *Sep. 4, 2012

(54) RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS

(75) Inventors: Yeonjoon Park, Yorktown, VA (US); Sang Hyouk Choi, Poquoson, VA (US); Glen C. King, Yorktown, VA (US); James R. Elliott, Yorktown, VA (US)

(73) Assignee: The United States of America, as represented by the Administrator of the National Aeronautics and Space Administration, Washington, DC (US)

( * ) Notice: Subject to any disclaimer, the term of this patent is extended or adjusted under 35 U.S.C. 154(b) by 989 days.

This patent is subject to a terminal disclaimer.

(21) Appl. No.: 12/288,379

(22) Filed: Oct. 20, 2008

(65) Prior Publication Data

US 2009/0206368 A1    Aug. 20, 2009

Related U.S. Application Data

(60) Provisional application No. 60/980,871, filed on Oct. 18, 2007, provisional application No. 60/980,881, filed on Oct. 18, 2007, provisional application No. 60/980,878, filed on Oct. 18, 2007, provisional application No. 60/980,880, filed on Oct. 18, 2007, provisional application No. 60/980,876, filed on Oct. 18, 2007, provisional application No. 60/980,870, filed on Oct. 18, 2007.

(51) Int. Cl.
*C30B 33/06* (2006.01)
*C30B 23/00* (2006.01)
*C30B 25/00* (2006.01)
*C30B 28/12* (2006.01)
*C30B 28/14* (2006.01)

(52) U.S. Cl. .............................................. 117/1; 117/84
(58) Field of Classification Search ................ 117/84, 117/1
See application file for complete search history.

(56) References Cited

U.S. PATENT DOCUMENTS

| 5,347,157 | A  | * | 9/1994  | Hung et al. .................. 257/627 |
| 6,524,935 | B1 |   | 2/2003  | Canaperi et al. |
| 8,044,294 | B2 | * | 10/2011 | Park et al. .................. 136/239 |
| 2003/0209191 | A1 | * | 11/2003 | Purdy ............................. 117/84 |
| 2007/0222034 | A1 |   | 9/2007  | Park et al. |
| 2009/0165837 | A1 | * | 7/2009  | Park et al. .................. 136/241 |

* cited by examiner

*Primary Examiner* — James McDonough
(74) *Attorney, Agent, or Firm* — Andrea Z. Warmbier; Thomas K. McBride, Jr.; Helen M. Galus (57) ABSTRACT

Growth conditions are developed, based on a temperature-dependent alignment model, to enable formation of cubic group IV, group II-V and group II-VI crystals in the [111] orientation on the basal (0001) plane of trigonal crystal substrates, controlled such that the volume percentage of primary twin crystal is reduced from about 40% to about 0.3%, compared to the majority single crystal. The control of stacking faults in this and other embodiments can yield single crystalline semiconductors based on these materials that are substantially without defects, or improved thermoelectric materials with twinned crystals for phonon scattering while maintaining electrical integrity. These methods can selectively yield a cubic-on-trigonal epitaxial semiconductor material in which the cubic layer is substantially either directly aligned, or 60 degrees-rotated from, the underlying trigonal material.

19 Claims, 7 Drawing Sheets

RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS

CROSS-REFERENCE TO RELATED APPLICATIONS

This application claims the benefit of the respective filing dates of, and incorporates by reference the entire respective disclosures of, the following commonly assigned U.S. Provisional Patent Applications: Ser. No. 60/980,871 filed on Oct. 18, 2007, Ser. No. 60/980,881 filed on Oct. 18, 2007, Ser. No. 60/980,878 filed on Oct. 18, 2007, Ser. No. 60/980,880 filed on Oct. 18, 2007, Ser. No. 60/980,876 filed on Oct. 18, 2007 and Ser. No. 60/980,870 filed Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,134, entitled HYBRID BANDGAP ENGINEERING FOR SUPER HETERO-EPITAXIAL SEMICONDUCTOR MATERIALS, AND PRODUCTS THEREOF; Ser. No. 12/254,016, entitled THERMOELECTRIC MATERIALS AND DEVICES; Ser. No. 12/254,017, entitled EPITAXIAL GROWTH OF CUBIC CRYSTALLINE SEMICONDUCTOR ALLOYS ON BASAL PLANE OF TRIGONAL OR HEXAGONAL CRYSTAL; Ser. No. 12/288,380, entitled X-RAY DIFFRACTION WAFER MAPPING METHOD FOR RHOMBOHEDRAL SUPER-HETERO-EPITAXY; and Ser. No. 12/254,150; entitled METHOD OF GENERATING X-RAY DIFFRACTION DATA FOR INTEGRAL DETECTION OF TWIN DEFECTS IN SUPER-HETERO-EPITAXIAL MATERIALS; each one claiming priority to the above-cited provisional applications.

ORIGIN OF THE INVENTION

The invention was made in part by employees of the United States Government and may be manufactured and used by or for the Government of the United States of America for governmental purposes without the payment of any royalties thereon or therefor.

BACKGROUND OF THE INVENTION

1. Field of the Invention

The present invention is in the field of semiconductor materials, and more particularly group IV, III-V and II-VI cubic crystalline semiconductor material (and alloys thereof) grown on trigonal substrates. More specifically, the invention concerns methods and conditions for creating substantially single crystalline cubic semiconductors in the [111]-orientation on the basal (0001) planes of trigonal crystal substrates.

2. Description of the Related Art

Silicon Germanium (SiGe) on sapphire is one of the important approaches to build Silicon Germanium On Insulator (SGOI) devices such as a high mobility transistor for K-band and higher frequency applications up to 116 GHz. Because sapphire is one of the best insulators, the high-frequency parasitic capacitance between the semiconductor layer and the substrate can be essentially eliminated. Many epitaxial growths using this approach utilize Silicon On Sapphire (SOS) and Silicon Germanium On Sapphire (SGOS) technologies which take advantage of the rectangular R-plane of sapphire aligned with the square-faced (001) plane or rectangle-faced (110) plane of the Si and Ge diamond structure. However, this approach often shows 90° rotated twin defects. Wafer bonding of SiGe on sapphire has also been used. On the other hand, growth of cubic SiGe layers on the trigonal (0001) plane, i.e. c-plane of sapphire has not been utilized for device fabrication so far due to the formation of 60° rotated twin defects.

While SiGe is desirable as a material for transistors and other microelectronic devices, SiGe can also be a good thermoelectric material that can be integrated into Si microelectronic circuits. Micro-coolers based on the super lattice of SiGe and SiGeC have shown substantial cooling power on the order of 1,000 Watt/cm$^2$. As explained in our disclosure regarding thermoelectric materials (which has been incorporated herein by reference), a high thermoelectric figure of merit ($ZT=S^2\sigma/k$) requires low thermal conductivity (k), high electrical conductivity ($\sigma$), and high Seebeck coefficient (S). While good semiconductor device materials require a single crystalline phase without defects, many good thermoelectric materials have electrically connected poly-type crystalline structures that scatter phonons, thus reducing thermal conductivity. For example, thermoelectric skutterudite material has three pnictogen square planes that can orient randomly. The growth of SiGe on trigonal (0001) plane of sapphire can scatter more phonons by utilizing the poly-type structures formed by twin crystals thus increasing the thermoelectric figure of merit by reducing thermal conductivity.

Despite these potential benefits, growing silicon germanium in the [111] direction on trigonally structured c-plane (0001) sapphire has been a challenge, because this atomic alignment allows poly-type crystalline structures with 60 degree-rotated twin defects as a result of stacking faults as well as twinning on the interface with the underlying trigonal substrate. The same considerations apply to cubic crystal structures of other group IV materials, as well as group III-V and II-VI materials, and alloys thereof.

For the above reasons, the single crystalline growth of cubic group IV, III-V and II-VI semiconductor material in diamond structure or cubic zinc blende structure (and alloys of such materials) on the basal plane of trigonal crystal substrate has been thought to be impossible or very difficult.

There is a pressing need, therefore, to develop fabrication conditions that allow the control of stacking and twinning in this class of materials.

SUMMARY OF THE INVENTION

It is an object of the invention to develop methods and conditions for controlling stacking faults and twin crystals in the growth in the [111] orientation of cubic crystalline group IV, III-V and II-VI materials (including alloys thereof) on the basal (0001) plane of trigonal substrates.

It is a further object of the invention to use such control techniques to provide semiconductor materials and devices comprising such materials wherein (on the one hand) the cubic semiconductor layer approximates a single crystal, or (on the other hand) reflects a polycrystalline structure, or reflects some other selected crystal configuration criterion.

To achieve these results, the present invention generally involves, in one embodiment, the use of a temperature-dependent alignment model to develop growth conditions to enable formation of cubic group IV, group III-V and group II-VI crystals (and crystals of alloys of such materials) in the [111] orientation on the basal (0001) plane of trigonal crystal substrates, controlled such that the volume percentage of primary twin crystal is reduced from about 40% to about 0.3%, compared to the majority single crystal. The control of stacking faults in this and other embodiments can yield single crystalline semiconductors based on these materials that are substantially without defects, or improved thermoelectric materials with twinned crystals for phonon scattering while maintaining electrical integrity. These methods can selectively yield a cubic-on-trigonal epitaxial semiconductor material in which the cubic layer is substantially either directly aligned, or 60 degrees-rotated from, the underlying trigonal material.

Other aspects and advantages of the invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 1 shows (a) trigonal primitive unit cell structure of sapphire, (b) diamond structure of SiGe, (c) rhombohedral alignment: the <111> direction of cubic crystal is aligned with <0001> direction of trigonal substrate, and (d) two possible in-plane azimuthal alignments inside rhombohedral alignment, view from [111] direction.

DETAILED DESCRIPTION OF THE INVENTION

The following is a detailed description of certain embodiments of the invention chosen to provide illustrative examples of how it may advantageously be implemented. The scope of the invention is not limited to the specific embodiments described, nor is it limited by any specific implementation, composition, embodiment or characterization depicted in the accompanying tables or drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used. That is, crystal planes are designated by numbers within "( )", groups of similar planes are designated by numbers within "{ }", direction or length is designated by numbers within "[ ]", and groups of similar directions are designated by numbers within "< >".

Figure 1A:
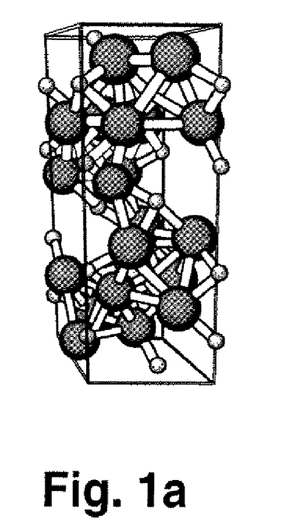
Figure 1B:
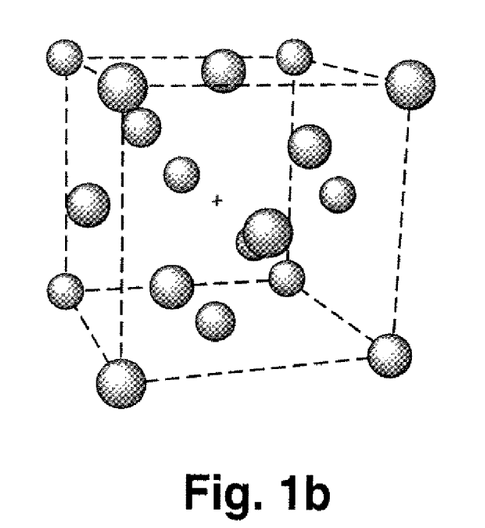
Figure 1C:
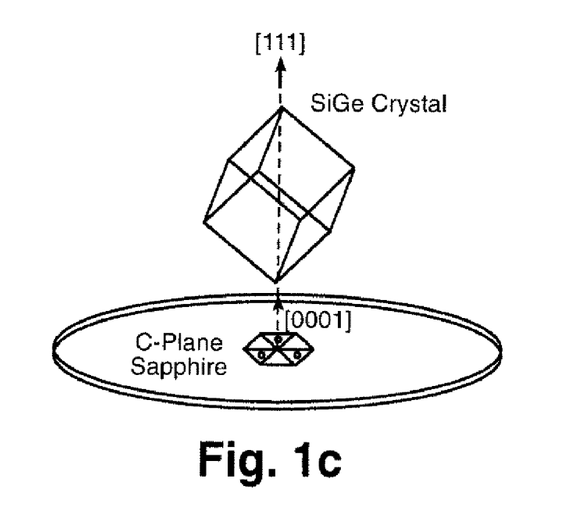
Figure 1D:
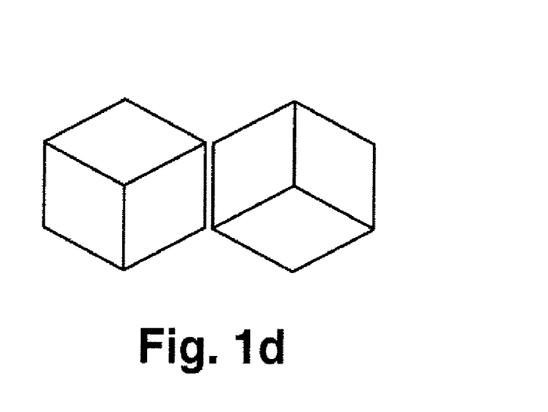

The crystal structures of sapphire and SiGe are shown in FIGS. 1(a) and (b) respectively. Efforts to grow silicon germanium in the [111] direction on trigonally structured c-plane (0001) sapphire as shown in FIG. 1(c) have met with impediments and only limited success. Conventionally, the single crystalline growth of group IV, III-V and II-VI semiconductor material (and alloys thereof) in diamond structure or cubic zinc blende structure on the basal plane of trigonal crystal substrate was thought to be impossible or very difficult. Rhombohedral alignment, i.e. aligning the [111] direction of a cubic structure to the [0001] direction of a trigonal structure, can have two possible azimuthal configurations as shown in FIG. 1(d). The two configurations are twin to each other (but different), and they can be formed by a stacking fault during the crystal growth process, or at the interface with the underlying trigonal material. This atomic alignment has conventionally only allowed poly-type crystalline structures with stacking faults on the (111) plane. We found that these difficulties in controlling the crystal growth process in these materials came in part from the lack of the proper macroscopic characterization tool to monitor the entire wafer.

The ability to measure and control stacking faults and twin crystals is important in two applications that are in some respects opposing in their requirements. For semiconductor device applications, good SiGe layers are desirable, with reduced amounts of stacking faults and micro twin defects. On the other hand, good thermoelectric materials require low thermal conductivity. A high density of stacking faults made by twinned SiGe layer can be one approach to lower the thermal conductivity.

In other disclosures that have been incorporated herein by reference, we provide two new X-ray diffraction methods as important non-destructive inspection tools that can enable the rhombohedral hetero-crystal-structure epitaxy of cubic semiconductors on the c-plane of the selected trigonal crystals. Using these methods, we have been able to develop growth conditions to enable the production of the desired new semiconductor materials. As explained in other disclosures incorporated herein by reference, rhombohedrally aligned, strained or lattice-matched layer(s) can be grown with various standard growth methods, including but not limited to, sputtering methods, Molecular Beam Epitaxy (MBE), Metal-Organic Chemical Vapor Deposition (MOCVD), MetalOrganic Chemical Vapor Phase Epitaxy (MOVPE), Hydride Vapor Phase Deposition (HVPE), Liquid Phase Epitaxy (LPE), Physical Vapor Deposition (PVD), and Pulsed Laser Deposition (PLD). To fabricate the final device structures, standard microfabrication technologies can be used, including but not limited to, lithography, etching, metallization, dopant diffusion/implantation and oxidation. The resulting cubic diamond semiconductor alloy on the trigonal substrate can be used "as is" or can be removed from the substrate after growth to a desired thickness. Such methods of removal are well known in the art and could include laser cutting, hydrogen cracking, etc., the choice of which is not a limitation of the present invention.

EXAMPLES

DC and RF-sputtering methods were used to grow a SiGe layer on c-plane sapphire. A 2-inch sapphire wafer was cleaned with acetone, iso-propanol, and deionized (DI)-water before transfer to a vacuum chamber. The sapphire wafer was baked at 200° C. to remove water vapors and then heated to 1,000° C. for a short time to remove any volatile contaminants. Substrate wafers are preferably cut to expose the basal plane, i.e. (0001) c-plane, but may be used with a small off-cut angle of up to about 10 degrees. The temperature was monitored by thermocouple measurement near the wafer holder.

The thermocouple growth temperature of a first series of SiGe layers on sapphire was measured at 820° C., but the actual temperature could have been less than the thermocouple temperature, because the infrared light passes the transparent sapphire.

The back-sides of a second series of sapphires were coated with thick carbon layers to achieve higher substrate temperature with the absorption of the infra-red radiation. The growth temperature of the second series was 850° C. This temperature was chosen after numerous different growth runs in order to illustrate sensitive changes in the primary twin crystal concentration with respect to the growth parameters.

Seven (7) sccm (standard cubic centimeters per minute) of high purity Argon gas was used in the sputtering process. The chamber pressure was maintained at 10 mtorr. In the first series, three SiGe samples were grown at 820° C. with different DC sputtering powers of 150 watts, 200 watts, and 300 watts. In the second series, two samples were grown at 850° C. with 200 watts and 300 watts.

An equal DC power was applied to Si and Ge target materials. The X-ray diffraction analysis of the SiGe (111) peaks shows that all the samples have the composition of $Si_{0.15}Ge_{0.85}$ due to the higher sputtering yield of Ge (in the terms of our other disclosures incorporated herein by reference, this SiGe composition reflects a strained lattice on the c-plane sapphire substrate, in Type B alignment). By increasing DC power, the kinetic energies of Si and Ge species and the overall flux of Si and Ge increased.

While depositing Si and Ge with the DC sputtering method, boron was co-sputtered and mixed into the SiGe layer as p-type dopant using the RF-sputtering gun. The RF-sputtering power of boron was only about 1-3 watts, which resulted in the heavy doping of above $10^{19}$/cm3.

After the growth was completed, the samples were analyzed with a 4-circle X-ray diffractometer and scanning electron microscope (SEM).

XRD Observations and Discussion

Figure 2:
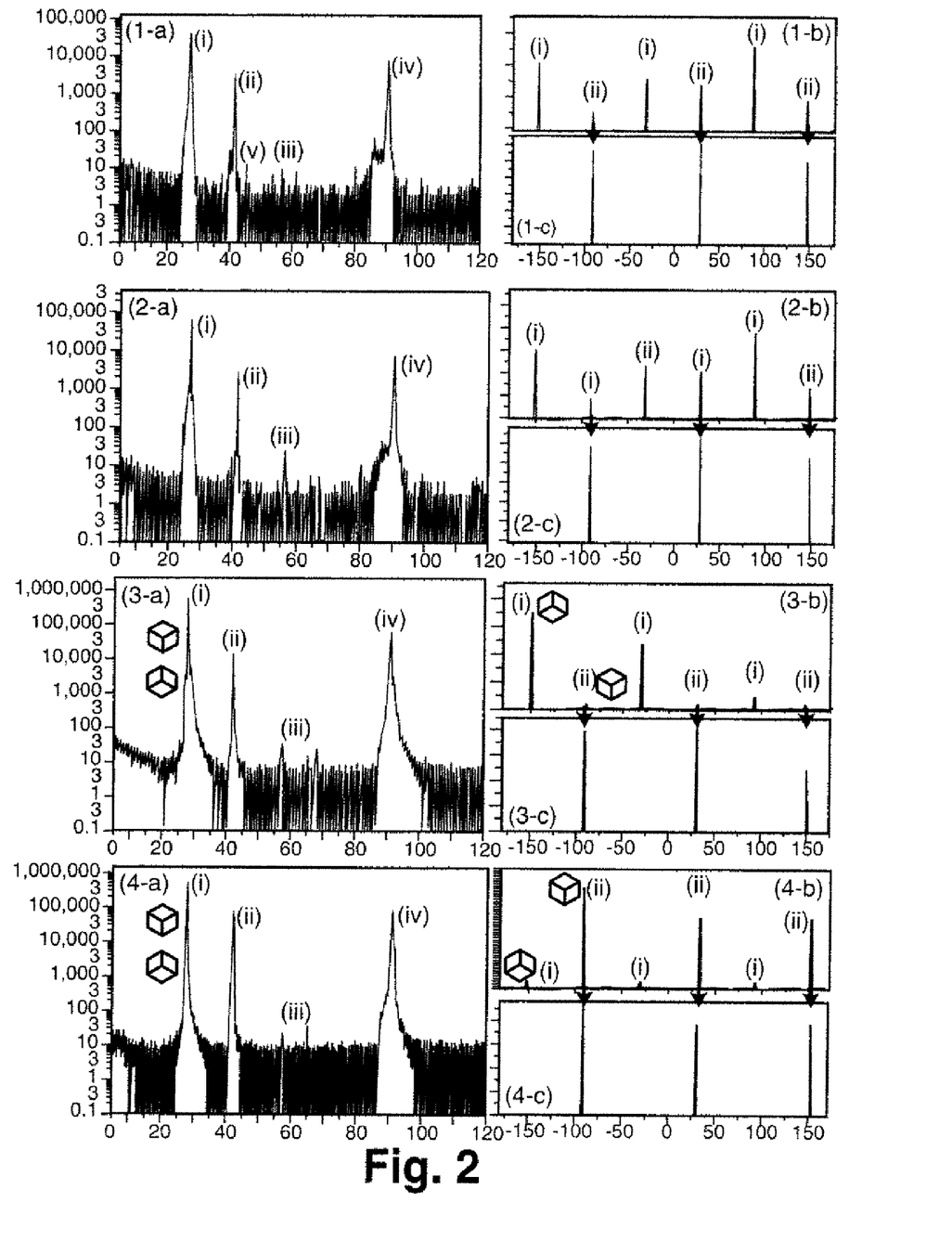
FIG. 2 shows X-ray diffraction measurement on four samples: samples (1), (2), and (3) grown below 820° C., and sample (4) grown at 850° C. Graph (a) shows θ-2θ scan in surface normal direction; graph (b) shows phi-scan of SiGe {220} peaks; and graph (c) shows phi-scan of sapphire {10-14} peaks for relative atomic alignment. Graph (1-b), (2-b), and (3-b) are in the linear scale and graph (4-b) is in the square root scale in order to show tiny twin peaks.

FIG. 2 shows the orientation dependent X-ray diffraction results of four SiGe samples. In FIG. 2, (1-a), (2-a), (3-a), and (4-a) show the 2θ-Ω scans of four samples in the surface normal direction. Peak (i) is SiGe (111), peak (ii) is sapphire (0006), peak (iii) is SiGe (113), peak (iv) is sapphire (0 0 0 12), and peak (v) is SiGe (220). The strong SiGe (111) peak indicates that majority of the SiGe layer was grown in [111] orientation on c-plane sapphire. In a separate rocking curve measurement, Full-Width-Half-Maximum (FWHM) of SiGe (111) peak was found to be 0.81°, 0.17°, 0.13°, and 0.15° respectively.

In order to check the distribution of SiGe crystal in azimuthal in-plane angles, we used phi-scan of SiGe {220} peaks and sapphire {10-14} peaks as shown in (1-b)-(4-b) and (1-c)-(4-c) in FIG. 2. Three {10-14} peaks show the trigonal space symmetry of a sapphire crystal. This method was reported to detect the concentration of twin crystals of zinc-blende structures in the case of homo-epitaxy of GaAs (111)B MBE growth (Y. Park, M. J. Cich, R. Zhao, P. Specht, E. R. Weber, E. Stach, and S. Nozaki, J. Vac. Sci. Technol. B 18, 1566-1571 (2000)) and hetero-epitaxy of hexagonal and cubic GaN growth on GaAs (111)B surface (S. Sanorpim, E. Takuma, R. Katayama, H. Ichinose, K. Onabe, and Y. Shiraki, Phys. Status Solidi B 240, 305-309 (2003)). Although four samples have similarly strong SiGe (111) peaks in the normal XRD scan, their phi-scans of SiGe{220} peaks show a large difference in the alignment and the ratio of majority single crystal. The majority peaks are noted as (i) in graphs (1-b), (2-b), and (3-b), and (ii) in graph (4-b). The minority primary twin crystal peaks that are rotated by 60 degrees are noted as (ii) in (1-b), (2-b), and (3-b) and (i) in (4-b). The ratios are 60:40 in (1-b), 83:17 in (2-b), 92:8 in (3-b), and 0.3:99.7 in (4-b).

For the samples grown under 820° C., the minority twin crystal's {220} peaks are always aligned with sapphire's {10-14} peaks as shown in (1-c), (2-c), and (3-c). For the same samples, the majority single crystal's {220} peaks are always aligned by 60° rotation from sapphire's {10-14} peaks. This tendency was reversed in the sample (4), which was grown above 850° C. In the graph (4-b) and (4-c), the strong majority peaks are directly aligned with sapphire {10-14} peaks. Small cube icons were inserted in the graph of sample (3) and (4) in order to show the meaning of each peak. This structure preference at high growth temperature was confirmed in numerous growth runs.

Figures 3A, 3B, 3C:
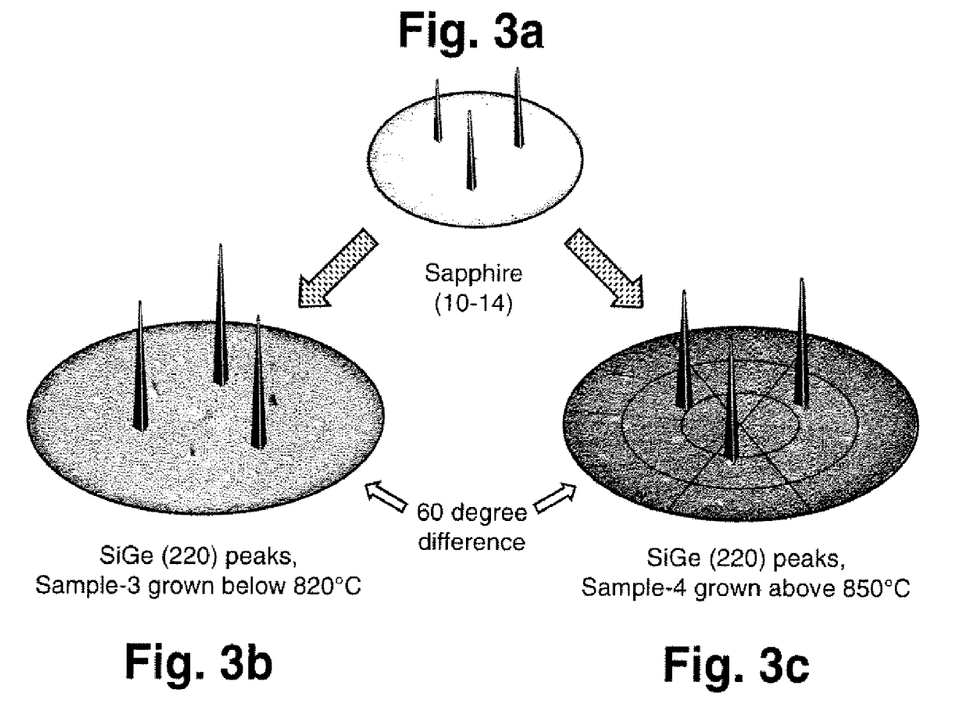
FIG. 3 shows Pole figures of SiGe {220} peaks with respect to the sapphire substrate.

FIG. 3 shows the pole figures of SiGe {220} peaks with respect to the sapphire substrate's {10-14} peaks. The strong three {220} peaks without other peaks indicate that the grown SiGe layer is close to single crystalline material. The 60° difference between two SiGe layers grown at different temperatures indicates that there exists a temperature dependent formation energy difference between majority single crystalline SiGe and minority twin crystalline SiGe on c-plane sapphire.

Figure 4A:
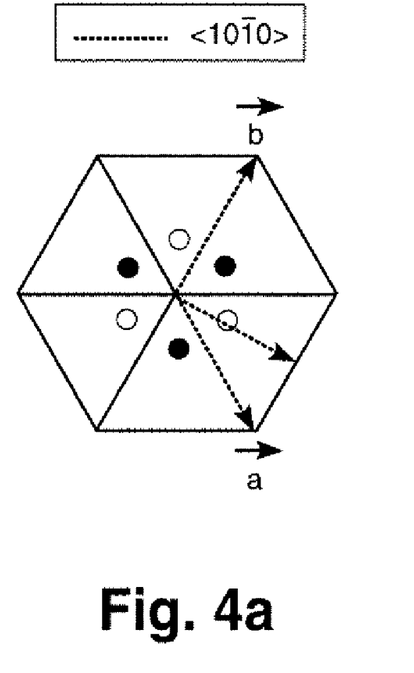
FIG. 4 shows a numerical representation of the same vector with respect to different basis vector sets.
Figure 4B:
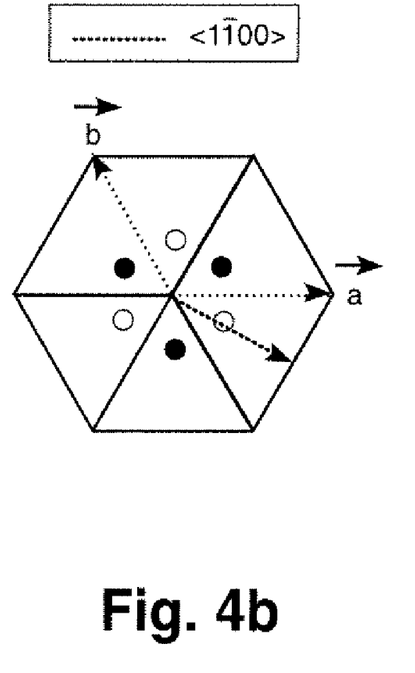

In the hexagonal coordinate description of trigonal crystal structure, there can be two different basis vector sets. For example, the same vector can be described as <10-10> with a basis vector set as shown in FIG. 4(a), or it can be described as <1-100> with another basis vector set as shown in FIG. 4(b). We followed the basis vector set in FIG. 4(a) in order to describe three strong XRD peaks of {10-14}. This basis vector set was chosen to be in accordance with the previous peak assignments in powder diffraction data of sapphire. (See Reference code 01-089-3072, International centre for diffraction data (ICDD), powder diffraction file-2 (2005).) In this basis vector set, {10-14} plane group contains three equivalent planes, (10-14), (-1104), and (0-114) which have strong X-ray diffraction peaks while another distinct 60-degree rotated {1-104} group contains (1-104), (-1014), and (01-14) planes that have no x-ray diffraction peaks. These numerical representations for two distinct 60-degree rotated groups are exchanged when a different basis vector set is used as shown in FIG. 4(b).

In order to confirm the XRD analysis of crystal orientation, additional measurements were made with SEM and Electron Back Scattered Diffraction (EBSD). EBSD uses a high-energy electron beam at a glancing angle to generate secondary electrons. When secondary electrons escape from the surface of a sample, they form a complex diffraction pattern, commonly known as a Kikuchi pattern. This diffraction pattern is developed by a bulk crystal structure at the e-beam spot. An electron-sensitive CCD detector at close proximity to the sample surface collects the secondary electron intensity and its spatial distribution, i.e. Kikuchi pattern. The analysis of this pattern reveals the crystal orientation and phase of bulk material at the e-beam irradiated spot. See W. Wu, L. J. Chen, J. Washburn, and G. Thomas, J. App. Phys. 45, 563-566 (1974); U. Konig and B. Davepon, Electrochimica Acta 47, 149-160 (2001).

Figure 5:
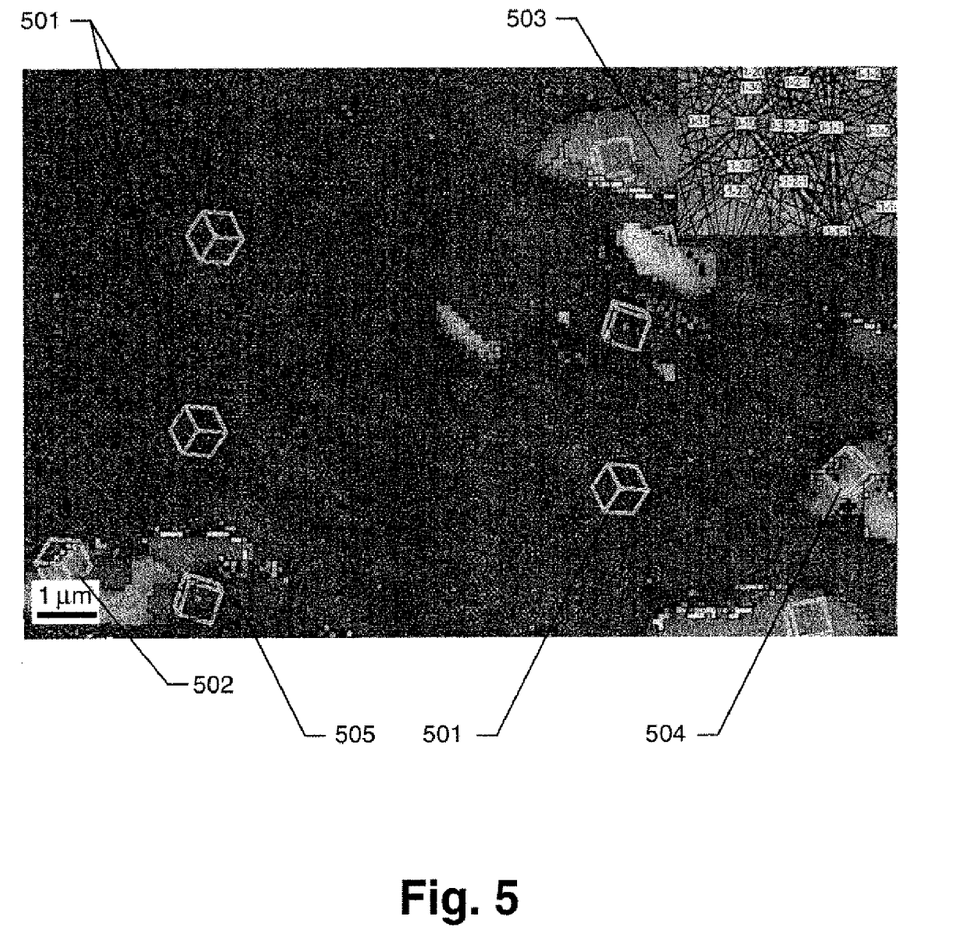
FIG. 5 is an SEM image of sample 3 with crystal orientation mapping as analyzed by EBSD. Region 501 is the majority single crystal domain. The inset picture is an EBSD analysis of Kikuchi pattern on one spot.

By scanning e-beam, a color coded SEM image can be obtained in which each color indicates a crystal domain of similar orientation as shown in FIG. 5, but in gray scale for purposes of this application, wherein different gray tones correspond to different colors. (The original color pictures corresponding to some of the present figures are available in the journal paper: Y. Park, G. C. King, S. H. Choi, Rhombohedral epitaxy of cubic SiGe on trigonal c-plane sapphire, Journal of Crystal Growth 310 (2008) 2724-2731, which is hereby incorporated herein by reference in its entirety.) This picture shows the EBSD analysis of crystal orientation domain in a small region (15 μm×10 μm) of sample 3. A few line-art cubic shapes are drawn to indicate crystal orientation of each color-domain with the same colored domain having similar crystal orientation. Inset picture shows the secondary electron diffraction pattern measured at one spot in this SEM image. In FIG. 5, the majority of the area is the domain (501) (originally blue-colored), which is a [111]-oriented majority single crystal region, while the small area (502) (originally green) is [111]-oriented minority primary-twin crystal region. In XRD analysis, the ratio of these two areas was 92:8. Therefore, the EBSD analysis confirms the result of XRD phi-scan analysis. The EBSD analysis also revealed additional regions (orange (503), brown (504), and violet (505)) in different crystal orientations which were not measured in XRD normal scan and phi-scan. These domains were identified as secondary and ternary twins, i.e. twin of twin crystals on other {111} planes with Σ9 and Σ27 boundaries. (E. Pihan, A. Focsa, A. Slaoui, and C. Maurice, Thin Solid Films 511 (2006) p. 15-20.) Since XRD phi-scan of SiGe {220} was intended to detect primary twin crystals, these secondary and ternary twin crystal regions (about 15% of the region) were not detected. However, EBSD confirms that about 85% of the entire region is [111]-oriented single crystal domain (blue color 501) with minor inclusion of primary twin crystal region (green color 502) as measured by XRD.

The spatial mapping of twin defects has been very difficult because only microscopic characterization tools such as Transmission Electron Microscope (TEM) and EBSD could detect the real space images but they were limited to only a few micrometers of the field of view. In an accompanying disclosure that has been incorporated herein by reference, we show a new XRD-based non-destructive spatial mapping method to detect the distribution of twin defects across the whole wafer with a high spatial resolution. This method uses a cubic semiconductor's asymmetric {440} peaks while scanning the wafer in X-Y direction under a narrowly masked X-ray beam for spatial resolution. It is also applicable to other cubic semiconductors such as other group IV and group III-V and II-VI semiconductor material (and alloys thereof) in diamond structure or cubic zinc blende structure.

Figure 6:
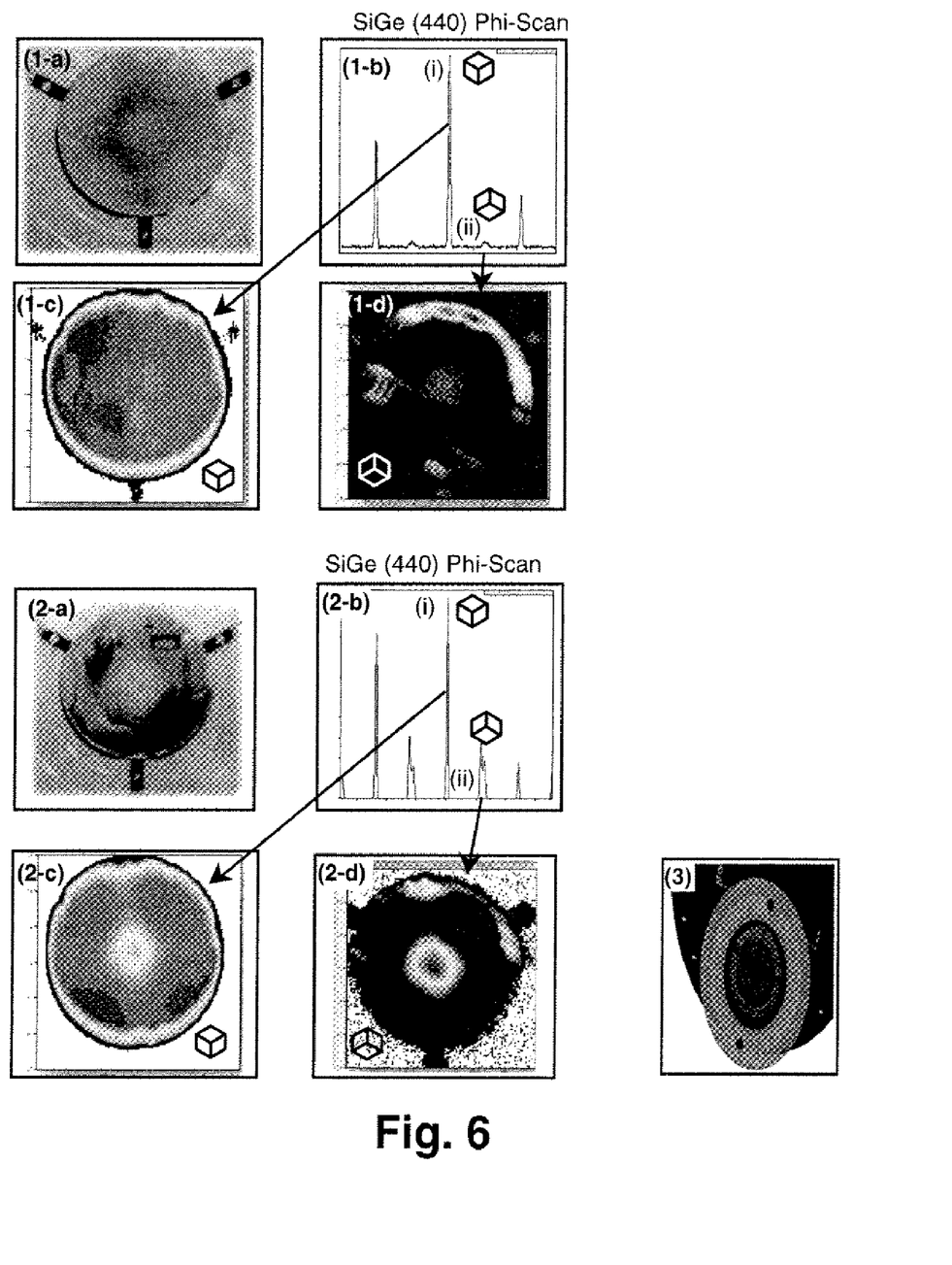
FIG. 6 shows an analysis of two SiGe samples: (1-a) photo of 94% single crystalline SiGe; (2-a) photo of SiGe layer with a mirror-like surface; (1-b) & (2-b) Phi scan of SiGe {440} peaks; (1-c) & (2-c) XY-wafer mapping with majority {440} peak marked with (i), shows the distribution of a single crystal; (1-d) & (2-d) XY-wafer mapping with minority {440} peak marked with (ii), shows the distribution of defect twin crystal; (3) photo of the sample holder, showing the (+) shaped thermal shadow in front of the substrate heater.

FIG. 6 shows X-ray diffraction wafer mapping result with SiGe {440} peaks instead of {220} peaks. For an isotropic uniform wafer mapping, we set sample-tilt Ψ angle (also known as χ angle)=0°. For $Si_{0.15}Ge_{0.85}$, we set the detector angle 2θ=101.57° for the SiGe {440} peak, and the sample goniometer angle Ω=θ+τ (inter planar angle between {440} and (111))=101.57°/2+35.264°=86.049°, which is very close to surface normal angle, 90°. With this configuration, the diffracted X-ray's exit angle from the surface is θ−τ=101.57°/2−35.264°=15.521°>0°. Therefore this configuration can be measured with a conventional X-ray diffraction setup. On the other hand, the SiGe {220} peak has a negative exit angle of diffracted X-rays, i.e. θ−τ=45.584°/2−35.264°=−12.472°<0° so that it cannot be measured with a conventional setup because there is no {220} diffracted X-ray beam above the sample surface in the ψ=0° set up.

In FIG. 6, (1-a) and (2-a) show the photos of two wafers, (1) 94% single crystalline wafer with a rough surface and (2) another wafer with a mirror-like surface. Both of the wafers were grown above 850° C. (1-b) and (2-b) show the phi scan of SiGe {440} peaks. By setting the phi angle of a wafer to one of the strong peaks and starting XY movement of a wafer with a narrow beam mask or crossed slit, the single crystalline maps (1-c) and (2-c) were obtained. By setting the phi angle to one of weak SiGe {440} peaks and moving the wafer into XY direction, the twin defect maps were obtained as shown in (1-d) and (2-d). In these mappings, a point X-ray source with a 5 mm beam mask was used. (1-c) and (1-d) show that an almost complete single crystalline SiGe layer was fabricated on the basal plane of trigonal sapphire although the surface looks rough. Only a small amount of twin defect is formed on the edge of a wafer. (2-c) and (2-d) show that four quadrant regions with the mirror-like surfaces are single crystalline SiGe layers without twin defects. The twin defects are concentrated in the (+) shaped region at the center. This (+) shaped region was the low temperature area under a thermal shadow created by the sample holder cage structure shown in the picture (3) of FIG. 6. Therefore, we conclude that a single crystalline SiGe layer with a mirror-like surface can be fabricated on the trigonal basal plane of sapphire with a uniform substrate heater without a thermal variation.

Figure 7:
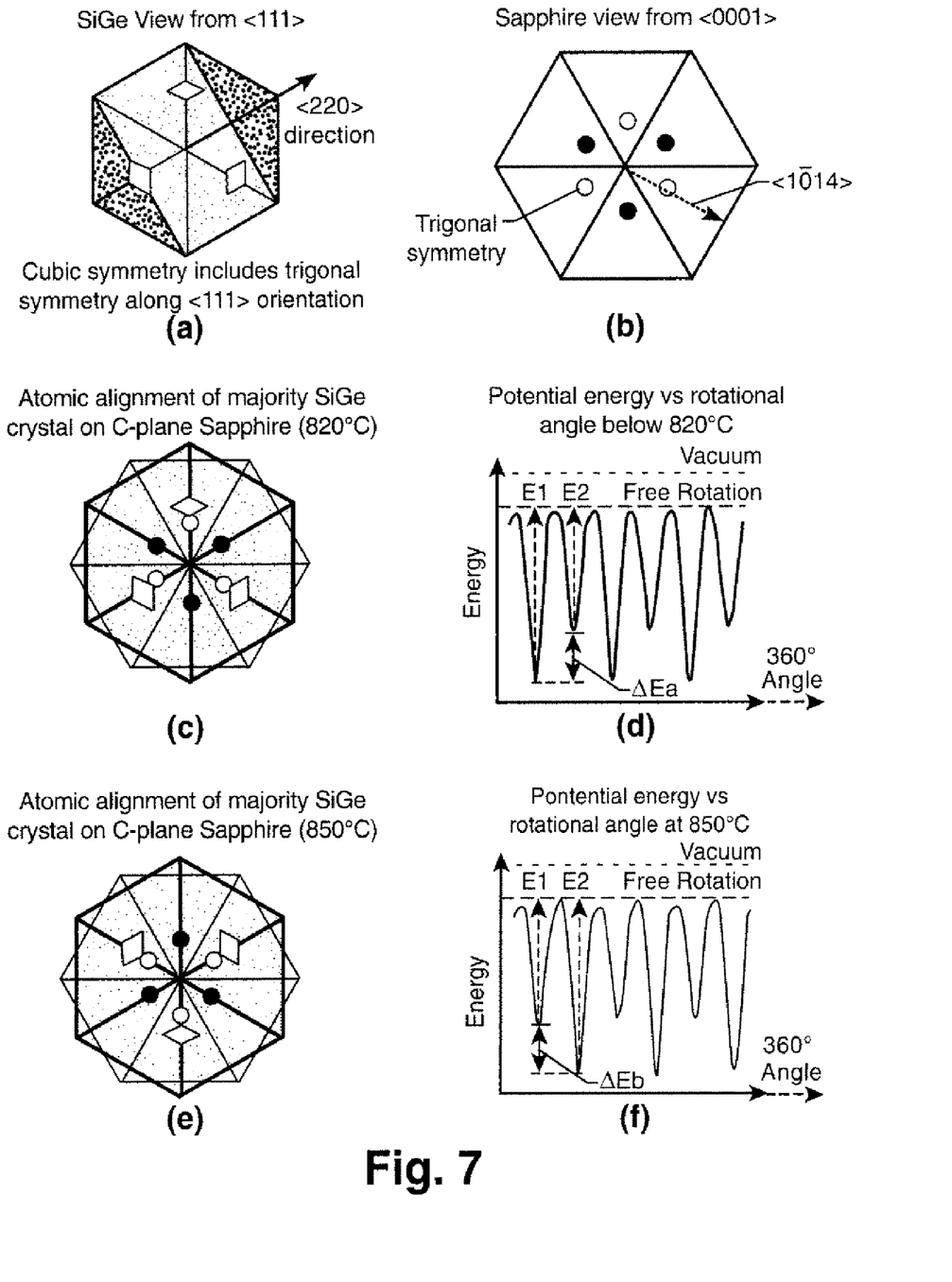
FIG. 7 shows the atomic alignment of SiGe majority domain crystals with respect to the c-plane sapphire.

By both XRD and EBSD analyses, we illustrate an azimuthal lattice-alignment model of majority single crystalline SiGe domain on c-plane sapphire as shown in FIG. 7. FIG. 7(a) shows three {100} facets as small parallelograms and indicates one of the {220} planes with an arrow. FIG. 7(b) shows trigonal symmetry of sapphire with three dots and indicates one of {10-14} planes with an arrow. When SiGe is grown on c-plane sapphire below 820° C., the <220> direction of majority single crystalline SiGe is 60° rotated from the <10-14> direction of sapphire such that they are azimuthally aligned as shown in FIG. 7(c). On the other hand, SiGe layer grown above 850° C., the <220> direction of majority single crystalline SiGe is directly aligned to the <10-14> direction of sapphire as shown in FIG. 7(e). Sample 3 and 4's symmetry-breaking ratio of 92:8 and 0.3:99.7 between majority single crystal and 60° rotated twin crystal indicates that there exists a large difference in the formation energy depending on the substrate temperature. This energy difference is plotted as ΔEa and ΔEb in FIGS. 7(d) and (f) as a molecular angular coordinate diagram. When the surface atom has enough kinetic energy, it can migrate from one site to the other and this case is noted as free rotation under vacuum level in FIGS. 7(d) and (f). Below 820° C., the dominant single crystalline SiGe has a deeper formation energy E1 than the formation energy E2 of twin crystalline SiGe such that E1(820° C.)>E2(820° C.). However, above 850° C. the formation energy E2 is larger than E1 such that E1(850° C.)<E2(850° C.).

Although we have not as yet determined the exact quantity of formation energy difference that depends on the substrate temperature, we conclude that these differences are large enough to fabricate high quality SiGe materials close to a single crystalline phase in the well-controlled growth conditions, based on the symmetry-breaking ratio in the integral XRD measurement of SiGe{220} and spatial wafer mapping of SiGe{440}. We propose that the best growth condition can be achieved by choosing the correct surface temperature and kinetic energy of incoming Si and Ge atomic flux so that the kinetic energy of surface atoms is between E1 and E2. For an example of high temperature growth above 850° C., when the kinetic energy of the surface atoms is higher than E1 but lower than E2, the accidental twin crystal is continuously annihilated but dominant single crystal is steadily formed. While previous studies were focused on SiGe on Si, our model shows the atomic alignment and formation energy difference at the interface of SiGe and c-plane sapphire. (Compare, T. S. Kuan and S. S. Iyer, App. Phys. Lett. 59, 2242-2244 (1991); K. E. Khor and S. Dassarma, J. Vac. Sci. Technol. B 9, 2198-2201 (1991); and K. E. Khor and S. Dassarma, Phys. Rev. B 43, 9992-9995 (1991).)

Thus, the foregoing shows that we fabricated a highly [111]-oriented $Si_{0.15}Ge_{0.85}$ layer on c-plane sapphire with a nearly single crystalline phase and twinned phase. Advanced XRD analyses showed the ratio of majority single crystal and 60° rotated crystal was controlled to 92%:8% below 820° C. and 0.3%:99.7% above 850° C. which indicates a large difference in the formation energy of two crystals on trigonal c-plane sapphire, depending on the substrate temperature. The high concentration of single crystalline phase SiGe layer grown on c-plane sapphire shows that [111] oriented single crystalline cubic semiconductors can be grown on the basal plane of selected trigonal substrates.

We used two twin-detection XRD methods, (1) integral measurement of average concentration of twin defects over a whole wafer—using {220} peaks, and (2) wafer mapping method with a high spatial resolution—using {440} peaks. Based on these XRD measurements, we proposed the temperature-dependent azimuthally-aligned atomic model of energetically favored SiGe domain on c-plane sapphire. The same relationships and methods should be equally applicable to any group IV, III-V and II-VI semiconductor material (and alloys thereof) in diamond structure or cubic zinc blende structure, on the basal plane of any trigonal crystal substrate.

The above results demonstrate, in accordance with the objects of the invention set out above, the ability to control the epitaxial growth to make a [111]-oriented single-crystalline-like layer, or a [111]-oriented highly-twinned layer, of group IV, III-V and II-VI semiconductor material (and alloys thereof) in diamond structure or cubic zinc blende structure, on the basal plane of any trigonal crystal substrate. The advanced XRD methods and fabricated materials described herein can help to build new rhombohedrally aligned cubic semiconductor materials on selected trigonal crystals for improved micro-electronic and thermoelectric devices.

Although the present invention has been described in detail, it should be understood that various changes, substitutions, and alterations may be readily ascertainable by those skilled in the art and may be made herein without departing from the spirit and scope of the present invention as defined by the following claims.

What is claimed as new and desired to be secured by Letters Patent of the United States is:

1. A semiconductor material comprising rhombohedrally aligned cubic semiconductor material (group IV, III-V, and II-VI), and alloys thereof, in diamond structure or cubic zinc-blende structure, on the basal plane of trigonal material layer or substrate with or without a small off-cut angle of less than about 10 degrees, wherein the cubic semiconductor material's three {220} peaks are directly aligned without any rotation to the underlying trigonal material's three-fold peaks.

2. A semiconductor material comprising rhombohedrally aligned cubic semiconductor material (group IV, III-V, and II-VI), and alloys thereof, in diamond structure or cubic zinc-blende structure, on the basal plane of trigonal material layer or substrate with or without a small off-cut angle of less than about 10 degrees, wherein the cubic semiconductor material's three {220} peaks are aligned with a 60° rotation to the underlying trigonal material's three-fold peaks.

3. The semiconductor material in accordance with claim 1 wherein said cubic material is an alloy of Silicon and germanium (SiGe), said trigonal substrate is c-plane sapphire and said three-fold peaks are the {10-14} peaks of said sapphire substrate.

4. The semiconductor material of claim 3 wherein the composition of said SiGe material by atomic ratio of silicon to germanium is about 0.15:0.85 ($Si_{0.15}Ge_{0.85}$).

5. The semiconductor material of claim 1 wherein said cubic material further comprises a dopant.

6. The semiconductor material of claim 3 wherein said SiGe material further comprises a dopant.

7. The semiconductor material of claim 6 wherein said dopant is a p-type dopant.

8. The semiconductor material of claim 7 wherein said p-type dopant is Boron.

9. The semiconductor material of claim 4 further comprising Boron as a p-type dopant at a concentration in excess of $10^{19}/cm^3$.

10. The semiconductor material in accordance with claim 2 wherein said cubic material is an alloy of Silicon and germanium (SiGe), said trigonal substrate is c-plane sapphire and said three-fold peaks are the {10-14} peaks of said sapphire substrate.

11. The semiconductor material of claim 10 wherein the composition of said SiGe material by atomic ratio of silicon to germanium is about 0.15:0.85 ($Si_{0.15}Ge_{0.85}$).

12. The semiconductor material of claim 2 wherein said cubic material further comprises a dopant.

13. The semiconductor material of claim 10 wherein said SiGe material further comprises a dopant.

14. The semiconductor material of claim 13 wherein said dopant is a p-type dopant.

15. The semiconductor material of claim 14 wherein said p-type dopant is Boron.

16. The semiconductor material of claim 11 further comprising Boron as a p-type dopant at a concentration in excess of $10^{19}/cm^3$.

17. A semiconductor device comprising a semiconductor material in accordance with claim 1.

18. The semiconductor device of claim 17 wherein said device is a Silicon Germanium On Insulator (SGOI) device.

19. The semiconductor device of claim 18 wherein said device is a high-mobility transistor for high-frequency applications.

* * * * *